United States Patent [19]

Drent et al.

[11] Patent Number: 5,177,253
[45] Date of Patent: Jan. 5, 1993

[54] PROCESS FOR THE PREPARATION OF ALPHA,BETA-OLEFINICALLY UNSATURATED COMPOUNDS

[75] Inventors: Eit Drent; Petrus H. M. Budzelaar; Willem W. Jager, all of Amsterdam, Netherlands

[73] Assignee: Shell Oil Company, Houston, Tex.

[21] Appl. No.: 668,846

[22] Filed: Mar. 13, 1991

[30] Foreign Application Priority Data

Jul. 3, 1990 [GB] United Kingdom ............... 9014724

[51] Int. Cl.$^5$ ............................................. C07C 67/36
[52] U.S. Cl. .................................... 560/207; 562/522; 562/890
[58] Field of Search ................. 560/207; 562/522, 890

[56] References Cited

U.S. PATENT DOCUMENTS 4,739,110  4/1988  Drent .................................. 560/207
5,028,734  7/1991  Drent .................................. 560/207

FOREIGN PATENT DOCUMENTS 186228  2/1986  European Pat. Off. .
271144  11/1987  European Pat. Off. .
305012  8/1988  European Pat. Off. .

Primary Examiner—Paul J. Killos

[57] ABSTRACT

A process for the preparation of an alpha,beta-olefinically unsaturated compound, which comprises reacting an acetylenically unsaturated compound with monoxide and a hydroxyl-containing compound in the presence of a catalyst system comprising:
(a) a source of a Group VIII metal cation,
(b) a source of an organic diphosphine having at least one of the phosphorus atoms substituted by an aromatic substituent containing an imino nitrogen atom, and
(c) a source of an anion.

17 Claims, No Drawings ic acid, for example an alkanoic acid such as acetic acid. Since halide ions can be corrosive, the source of a Group VIII metal cation is preferably not a halide.

PROCESS FOR THE PREPARATION OF ALPHA,BETA-OLEFINICALLY UNSATURATED COMPOUNDS

FIELD OF THE INVENTION

The present invention relates to a process for the preparation of alpha,beta-olefinically unsaturated compounds.

BACKGROUND OF THE INVENTION

It is well known that alpha,beta-olefinically unsaturated compounds may be prepared by carbonylating acetylenically unsaturated compounds with hydroxyl-containing compounds. The type of alpha,beta-olefinically unsaturated compound obtained depends upon the type of hydroxyl-containing compound used. Thus, if a carboxylic acid is used, the product is a carboxylic anhydride; if an alcohol is used, the product is a carboxylic ester; and if water is used, the product is a carboxylic acid. For example, the commercially important monomer, methyl methacrylate, may be prepared by carbonylating propyne with methanol.

One process for the preparation of alpha,beta-olefinically unsaturated compounds is disclosed in European Patent No. EP-A1-0186228. The process comprises reacting an acetylenically unsaturated compound with carbon monoxide and water or an alcohol in the presence of a catalyst system formed by combining a palladium (II) compound, an organic phosphine and a non-halogenic acid. It is apparent from the Examples in the patent specification that this process proceeds with a good reaction rate and good selectivity.

European Patent No. EP-A2-0271144 also discloses a process for the preparation of alpha,beta-olefinically unsaturated compounds. The process comprises reacting an acetylenically unsaturated compound with carbon monoxide and a hydroxyl-containing compound in the presence of a catalyst system comprising a palladium compound, a protonic acid and an organic monophosphine having three aromatic substituents at least one of which contains a nitrogen atom. The processes exemplified in the patent specification proceed with a very high reaction rate and high selectivity.

It has now been found that alpha,beta-olefinically unsaturated compound may be prepared with a good reaction rate and high selectivity using a particular organic diphosphine.

SUMMARY OF THE INVENTION

The present invention therefore provides a process for the preparation of an alpha,beta-olefinically unsaturated compound, which comprises reacting an acetylenically unsaturated compound with carbon monoxide and a hydroxyl-containing compound in the presence of a catalyst system comprising:
(a) a source of a Group VIII metal cation,
(b) a source of an organic diphosphine having at least one of the phosphorus atoms substituted by an aromatic substituent containing an imino nitrogen atom, and
(c) a source of an anion.

It is surprising that alpha,beta-olefinically unsaturated compounds may be prepared with a good reaction rate and high selectivity using a phosphine which contains more than one phosphorus atom.

DESCRIPTION OF THE PREFERRED EMBODIMENTS

Without wishing to be bound by any theory, it is believed that the active catalyst species in the catalyst system is a cationic complex of the Group VIII metal with the phosphine. Accordingly, the catalyst system employed in the process according to the invention must comprise a source of a Group VIII metal cation, a source of the phosphine and a source of an anion.

The source of a Group VIII metal cation is preferably a salt of the Group VIII metal. Examples of salts include salts of nitric acid; sulfuric acid; sulfonic acids, for example chlorosulfonic acid, methanesulfonic acid, t-butylsulfonic acid, p-toluenesulfonic acid or a sulphonated ion exchange resin; and a carboxylic acid, for example an alkanoic acid such as acetic acid. Since halide ions can be corrosive, the source of a Group VIII metal cation is preferably not a halide.

It will be appreciated that when the source of a Group VIII metal cation is a salt of a Group VIII metal, it will also be a source of an anion.

It will also be appreciated that when the source of a Group VIII metal cation is a salt of a Group VIII metal, the Group VIII metal may be present in a complex, for example with a phosphine. The source of a Group VIII metal cation may therefore also be a source of an organic diphosphine having at least one of the phosphorus atoms substituted by an aromatic substituent containing an imino nitrogen atom.

The source of a Group VIII metal cation may also be the metallic element or a compound of a Group VIII metal other than a salt. For example it may be an oxide or a zero valent complex with a ligand such as a phosphine or carbon monoxide. When the source of a Group VIII metal is not a salt, it should be used with a protonic acid. It will be appreciated that the protonic acid will also be a source of an anion.

The Group VIII metal is preferably nickel palladium or platinum. Very high reaction rates have been obtained using palladium. Accordingly, the Group VIII metal is most preferably palladium.

The quantity of the source of a Group VIII metal cation is not critical. Preferably it is sufficient to provide in the range of from about $10^{-7}$ to about $10^{-1}$ gram atoms of Group VIII metal per mole of acetylenically unsaturated compound, more preferably from about $10^{-6}$ to about $10^{-2}$.

The source of an organic diphosphine having at least one of the phosphorus atoms substituted by an aromatic substituent containing an imino nitrogen atom is conveniently the phosphine itself, or an acid addition salt of the phosphine. However as mentioned hereinabove, it may also be a complex of the phosphine with the Group VIII metal.

Preferably, both of the phosphorus atoms of the organic diphosphine are substituted by at least one aromatic substituent containing an imino nitrogen atom.

It will be appreciated that both of the phosphorus atoms may be substituted by the same aromatic substituent containing an imino nitrogen atom, as for example in 2,5-bis(diphenylphosphino)pyridine.

The organic diphosphine used in the process according to the invention preferably has the general formula:

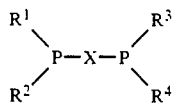 (I)

in which at least one of $R^1$, $R^2$, $R^3$ and $R^4$ represents an aromatic substituent containing an imino nitrogen atom, the remainder of $R^1$, $R^2$, $R^3$ and $R^4$ independently represent an optionally substituted hydrocarbyl or heterocyclic group, and X represents a divalent bridging group containing from 1 to 10 atoms in the bridge.

As used herein, the term "imino nitrogen atom" means a nitrogen atom which may be represented in the structural formula of the aromatic substituent containing it by the formula:

For example, if the aromatic substituent is a pyridyl group, the structural formula of the aromatic substituent is:

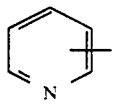

The aromatic substituent which contains an imino nitrogen is preferably a 6-membered ring containing one, two or three nitrogen atoms. The aromatic substituent may itself be optionally substituted.

When a substituent is said to be optionally substituted in this specification unless stated otherwise, the substituent may be unsubstituted or substituted by one or more substituents. Examples of suitable substituents include halogen atoms, alkyl groups; alkoxy groups; haloalkyl groups; haloalkoxy groups; acyl groups; acyloxy groups; amino groups, preferably alkyl or dialkylamino groups; hydroxy groups; nitrile groups; acylamino groups; and aromatic hydrocarbyl groups.

A hydrocarbyl group may be an aliphatic hydrocarbyl group or an aromatic hydrocarbyl group.

An aliphatic hydrocarbyl group is preferably an alkyl group, for example a $C_{1-10}$ alkyl group, such as methyl, ethyl, propyl or butyl; or a cycloalkyl group, for example a $C_{3-6}$ cycloalkyl group, such as cyclopentyl or cyclohexyl.

An aromatic hydrocarbyl group is preferably a phenyl group.

A heterocyclic group may be, for example, a 5- or 6-membered heterocyclic ring containing one or more oxygen, sulfur or nitrogen atoms, such as a furanyl or thiophenyl group.

A halogen atom, as such or in a haloalkyl group, is preferably a fluorine, chlorine or bromine atom.

An acyl group in an acyl, acyloxy or acylamino group is preferably a $C_{2-5}$ alkanoyl group such as acetyl.

Examples of aromatic substituents containing an imino nitrogen atom are pyridyl, pyrazinyl, quinolyl, isoquinolyl, pyrimidinyl, pyridazinyl, cinnolinyl, triazinyl, quinoxalinyl, and quinazolinyl. Preferred substituents are pyridyl and pyrimidyl.

An imino nitrogen atom in an aromatic substituent containing an imino nitrogen atom is preferably connected to a phosphorus atom through one, or less preferably two linking carbon atoms. For example, if the aromatic substituent is a pyridyl group, it is preferably connected through the carbon atom at the 2- or 3-position in the pyridyl group, more preferably at the 2-position. Accordingly, examples of preferred aromatic substituents containing an imino nitrogen atom are 2-pyridyl; 2-pyrazinyl; 2-quinolyl; 1-isoquinolyl; 3-isoquinolyl; 2-pyrimidinyl; 3-pyridazinyl; 3-cinnolinyl; 2-triazinyl; 2-quinoxalinyl; and 2-quinazolinyl. 2-Pyridyl and 2-pyrimidyl are particularly preferred.

The bridging group represented by X is preferably a hydrocarbon, an ether or a thio-ether residue. For example, the bridging group may be an alkylene chain which is optionally interrupted by one or more oxygen and/or sulphur atoms, as in:

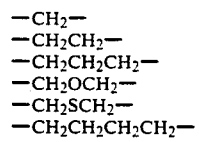

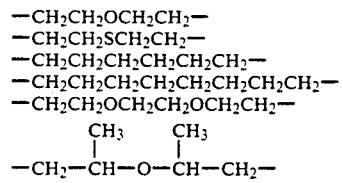

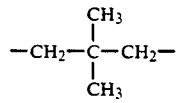

It may also be a silane residue, as in

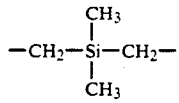

The bridging group preferably contains from 2 to about 8 atoms in the bridge, more preferably from 3 to about 5 atoms. For example, when the bridging group is a propane residue, the bridge contains 3 atoms.

Particularly high reaction rates have been obtained using organic diphosphines of general formula (I) in which X represents a dialkyl ether residue. Accordingly, the use of such compounds is preferred in the process according to the invention.

The remainder of $R^1$, $R^2$, $R^3$ and $R^4$ are preferably alkyl or optionally substituted phenyl groups. Most preferably they are optionally substituted phenyl groups.

Examples of organic diphosphines which may be used in the process according to the invention are:
bis[(2-pyridyl)phenylphosphino]methane,
1,2-bis[(2-pyridyl)phenylphosphino]ethane,
1,3-bis[(2-pyridyl)phenylphosphino]propane,
1,5-bis[(2-pyridyl)phenylphosphino]-3-oxapentane,
1,8-bis[(2-pyridyl)phenylphosphino]-3,6-dioxaoctane,
1,3-bis[(2-pyridyl)butylphosphino]propane, and
1,3-bis[di-(2-pyridyl)phosphino]propane.

The ratio of the number of moles of organic diphosphine per gram atom of Group VIII metal is preferably in the range of from about 0.75 to about 10, more preferably from about 0.9 to about 5, especially from about 1 to about 3. It is a particular advantage of the process according to the invention that only a very small quantity of phosphine is required.

The source of an anion used in the process according to the invention is preferably a protonic acid. However, as mentioned hereinabove, it may also be a salt of a Group VIII metal. It may also be a salt of another transition metal, for example vanadium, chromium, manganese, copper or silver.

Preferably, the anion is a non- or weakly-coordinating anion: that is to say an anion which does not or only weakly coordinates with the Group VIII metal cation.

Examples of non-coordinating anions are anions derived from acids having a pKa $<4$, preferably $<2$, more preferably $<1$ (measured at 18° C. in aqueous solution), except for hydrohalic acids.

For example, the anion may be derived from nitric acid; sulfuric acid; a sulfonic acid such as fluorosulfonic acid, chlorosulfonic acid, methanesulfonic acid, 2-hydroxypropanesulfonic acid, t-butylsulfonic acid, p-toluenesulfonic acid, benzenesulfonic acid, 1-naphthalenesulfonic acid, trifluoromethanesulfonic acid or a sulfonated ion exchange resin; a perhalic acid such as perchloric acid; a perfluorinated carboxylic acid such as trifluoroacetic acid; orthophosphoric acid; a phosphonic acid such as benzenephosphonic acid; or an acid derived by the interaction of a Lewis acid, such as $BF_3$, $AsF_5$, $SbF_5$, $TaF_5$ or $NbF_5$, with a Broensted acid, such as HF (e.g. fluorosilicic acid, $HBF_4$, $HPF_5$ and $HSbF_6$). Particularly good results have been obtained using a sulfonate as the anion.

It will be appreciated that when using a Group VIII metal salt of a weak acid, such as acetic acid, the addition of a strong acid such as a sulphonic acid will generate a salt of the Group VIII metal with the stronger acid, and the weak acid.

Organic diphosphines having at least one of the phosphorus atoms substituted by an aromatic substituent containing an imino nitrogen atom may be prepared, for example, according to the methods described in European Patent No. EP-A2-0305012. Thus, for example, they may be prepared by reacting an appropriate alkali metal phosphide with an appropriate dihalo compound.

The catalyst system used in the process according to the invention may be homogeneous or heterogeneous. Preferably, it is homogeneous.

The catalyst system according to the invention is constituted in a liquid phase. The liquid phase may conveniently be formed by one or more of the reactants with which the catalyst system is to be used. Alternatively, it may be formed by a solvent. It may also be formed by one of the components of the catalyst system.

The acetylenically unsaturated compound is preferably a substituted or unsubstituted alkyne having from 2 to about 20, especially from about 3 to about 10 carbon atoms per molecule. It may contain one or more acetylenic bonds, for example one, two or three acetylenic bonds.

The acetylene may be substituted by, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols such as, for example, 3-butyn-1-ol, 4-pentyn-1-ol or 3-pentyn-1-ol. Thus 3-butyn-1-ol may be converted into a-methylene-c-butyrolactone.

Examples of suitable alkynes are: ethyne, propyne, phenylethyne, 1-butyne, 2-butyne, 1-pentyne, 1-hexyne, 1-heptyne, 1-octyne, 2-octyne, 4-octyne, 1.7-octadiyne, 5-methyl-3-heptyne, 4-propyl-2-pentyne, 1-nonyne, benzylethyne and cyclohexylethyne.

The hydroxyl-containing compound is preferably an alcohol, water or a carboxylic acid.

Any alcohol used may be aliphatic, cycloaliphatic or aromatic and may carry one or more substituents. The alcohol preferably comprises up to 20 carbon atoms per molecule. It may be, for example, an alkanol, a cycloalkanol or a phenol. One or more hydroxyl groups may be present, in which case several products may be formed, depending on the molar ratio of the reactants used.

Examples of suitable alkanols include methanol, ethanol, 1-propanol, 2-propanol, 1-butanol, 2-butanol, 2-methylpropan-1-ol, and 2-methylpropan-2-ol.

Examples of suitable phenols include phenol, alkylphenols, catechols, and 2,2-bis(4-hydroxyphenyl)propane.

Other examples of alcohols include polyvalent alcohols, in particular lower sugars such as glucose, fructose, mannose, galactose, sucrose, aldoxose, aldopentose, altrose, allose, talose, gulose, idose, ribose, arabinose, xylose, lyxose, erythrose or threose, cellulose, starch, benzyl alcohol, 2,2-bis(hydroxymethyl)-1-butanol, diacetone D-glucose, stearyl alcohol, cyclohexanol, ethylene glycol. 1.2-propanediol, 1,4-butanediol, polyethyleneglycol, glycerol and 1,6-hexanediol.

The process according to the present invention can be carried out using a wide variety of carboxylic acids. For example, the carboxylic acids may be aliphatic, cycloaliphatic or aromatic and may carry one or more substituents, such as those named in connection with the acetylenically unsaturated compounds.

Carboxylic acids preferably used in the process according to the invention include those containing up to 20 carbon atoms. One or more carboxylic acid groups may be present, thus allowing various products as desired, depending on the molar ratio of the reactants used. The carboxylic acids may, for example, be alkanecarboxylic acids or alkenecarboxylic acids. Examples of carboxylic acids are: formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

It will be appreciated that the acetylenically unsaturated compound and the hydroxyl-containing compound may be the same compound.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

It is not essential to use a separate solvent in the process according to the invention.

A large excess of the product or of one of the reactants, for example an alcohol, can often form a suitable liquid phase. In some cases, however, it may be desirable to use a separate solvent. Any inert solvent can be used for that purpose. Said solvent may, for example, comprise sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone, ketones such as acetone or methyl isobutyl ketone and ethers such as anisole, 2,5,8-trioxanone (also referred to as diglyme), diphenyl ether and diisopropyl ether, or an amide such as dimethylacetamide or N-methylpyrrolidone.

The process according to the present invention is conveniently effected at a temperature in the range of from about 10° C. to about 200° C., in particular from about 20° C. to about 100° C.

The process according to the invention is preferably effected at a pressure of from about 1 to about 70 bar. Pressures higher than about 100 bar may be used, but are generally economically unattractive on account of special apparatus requirements.

The molar ratio of the hydroxyl-containing compound to the acetylenically unsaturated hydrocarbon may vary between wide limits and generally lies within the range of about 0.01:1 to about 100:1.

The process according to the invention may be operated batchwise or continuously.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5 vol %.

Since allenes have been found to inhibit the carbonylation reaction, it is preferred to use a feedstock of acetylenically unsaturated compound that is substantially free of allenes. In the Examples given below, the propyne contained less than 0.5% allene.

The invention will now be illustrated by the following Preparations and Examples which are provided for illustrative purposes and are not intended to be construed as limiting the scope of the invention.

Preparation of 1,3-bis[(2-pyridyl)butylphosphino]propane 5.9 ml of a 1.6 molar solution of n-butyllithium in n-hexane was added with stirring over a period of 10 minutes to a solution of 2.4 g of bis(2-pyridyl)phenylphosphine in 20 ml tetrahydrofuran which had been cooled to −80° C. The temperature of the reaction mixture was allowed to rise to room temperature, and was then cooled to −40° C. A solution of 0.96 g 1,3-dibromopropane in 10 ml tetrahydrofuran was then added with stirring. After the temperature of the reaction mixture had risen to room temperature, the solvents were removed under reduced pressure. Then, 25 ml diethylether and 10 ml water were added. After 10 minutes stirring, the organic layer was removed and the water layer was extracted with 10 ml diethylether. The organic liquids were combined and the solvent was removed under reduced pressure. NMR analyses showed that the remaining liquid consisted of a 1:2 molar mixture of 1,3-bis[(2-pyridyl)butylphosphino]propane and 2-phenylpyridine. 1,3-bis[(2-pyridyl)butylphosphino]propane was distilled from this mixture.

Preparation of 1,3-bis[di-(2-pyridyl)phosphino]propane 13.2 g of tris(2-pyridyl)phosphine and 0.7 g lithium in 100 ml tetrahydrofuran (THF) were stirred at room temperature for three days. Then, 5.0 g of 1,3-dibromopropane in 20 ml of THF were added over 15 minutes. After 2 hours under stirring, THF was distilled off, after which water and dichloromethane were added. The dichloromethane layer was separated and evaporated. The residual product was taken up in a warm 1:1 mixture of dichloromethane and hexane, from which 10 g of a viscous liquid was isolated. This was shown to be 95% pure 1,3-bis[di-(2-pyridyl)phosphino]propane by $^{31}$P NMR.

EXAMPLE 1

A 250 ml magnetically-stirred stainless steel autoclave was successively filled with 0.1 mmol palladium (II) acetate, 0.12 mmol bis[(2-pyridyl)phenylphosphino]propane, 1 mmol trifluoromethanesulfonic acid and 50 ml methanol. Air was then evacuated from the autoclave, and then 30 ml propyne was added. Carbon monoxide was then added to a pressure of 40 bar. The autoclave was then sealed and heated to a temperature of 70° C. After the reaction had ended, a sample of the contents of the autoclave was analysed by gas liquid chromatography. From the results of the analysis, the selectivity to methyl methacrylate (based upon converted propyne) was calculated to be 97.5%, and the mean conversion rate was calculated to be 500 mol propyne/gram atom Pd/hour.

COMPARATIVE EXAMPLE 1

A 250 ml magnetically-stirred stainless steel autoclave was successively filled with 0.5 mmol palladium (II) acetate, 0.6 mmol bis-1,3-(diphenylphosphino)propane, 1 mmol p-toluenesulfonic acid and 50 ml methanol. Air was then evacuated from the autoclave, and then 30 ml propyne was added. Carbon monoxide was then added to a pressure of 40 bar. The autoclave was then sealed and heated to a temperature of 115° C. After the reaction had ended, a sample of the contents of the autoclave was analysed by gas liquid chromatography. From the results of the analysis, the selectivity to methyl methacrylate (based upon converted propyne) was calculated to be only 85%, and the mean conversion rate was calculated to be only 30 mol propyne/gram atom Pd/hour.

EXAMPLE 2

A 250 ml magnetically-stirred stainless steel autoclave was successively filled with 0.1 mmol palladium (11) acetate, 0.12 mmol bis[(2-pyridyl)phenylphosphino]propane, 0.2 mmol p-toluenesulfonic acid, 50 ml methanol and 10 ml phenylethyne. Air was then evacuated from the autoclave, and then carbon monoxide was added to a pressure of 40 bar. The autoclave was then sealed and heated to a temperature of 60° C. After the reaction had ended, a sample of the contents of the autoclave was analysed by gas liquid chromatography.

From the results of the analysis, the selectivity to methyl phenylacrylate (based upon converted propyne) was calculated to be 99%, and the mean conversion rate was calculated to be >1000 mol phenylethyne/gram atom Pd/hour.

EXAMPLE 3

The method of Example 2 was repeated, but using 30 ml t-butanol instead of 50 ml methanol, and 30 ml phenylethyne. The selectivity to t-butyl phenylacrylate was calculated to be 99%, and the mean conversion rate was calculated to be 600 mol phenylethyne/gram atom Pd/hour.

EXAMPLE 4

The method of Example 3 was repeated, but using 0.12 mmol 1,3-bis[di-(2-pyridyl)phosphino]propane instead of 0.12 mmol bis[(2-pyridyl)phenylphosphino]propane, and 0.2 mmol methane sulfonic acid instead of 0.2 mmol p-toluenesulfonic acid. The selectivity to t-butyl phenylacrylate was calculated to 99%, and the mean conversion rate was calculated to be 200 mol phenylethyne/gram atom Pd/hour.

EXAMPLE 5

The method of Example 3 was repeated, but using 0.2 mmol t-butylsulfonic acid instead of 0.2 mmol p-toluenesulfonic acid, and heating to 70° C. instead of 60° C. The selectivity to t-butyl phenylacrylate was calculated to be 98%, and the mean conversion rate was calculated to be 600 mol phenylethyne/gram atom Pd/hour.

EXAMPLE 6

The method of Example 3 was repeated, but using 0.2 mmol methanesulfonic acid instead of 0.2 mmol p-toluenesulfonic acid, 40 ml isopropanol instead of 30 ml t-butanol, and heating to 50° C. instead of 60° C. The selectivity to isopropyl phenacrylate was calculated to be 99%, and the mean conversion rate was calculated to be 800 mol phenylethyne/gram atom Pd/hour.

EXAMPLE 7

The method of Example 6 was repeated, but using 30 ml methanol instead of 40 ml isopropanol, and heating to 40° C. instead of 50° C. The selectivity to methyl phenylacrylate was calculated to be 99%, and the mean conversion rate was calculated to be 600 mol phenylethyne/gram atom Pd/hour.

EXAMPLE 8

The method of Example 7 was repeated, but using 0.12 mmol bis[(2-pyridyl)butylphosphino]propane instead of 0.12 mmol bis[(2-pyridyl)phenylphosphino]propane. The selectivity to methyl phenylacrylate was calculated to be 98%, and the mean conversion rate was calculated to be 500 mol phenylethyne/gram atom Pd/hour.

EXAMPLE 9

The method of Example 1 was repeated, but using 1 mmol methanesulfonic acid instead of 1 mmol trifluoromethanesulfonic acid, 15 ml propyne instead of 30 ml propyne, and heating to 75° C. instead of 70° C. The selectivity to methyl methacrylate was calculated to be 97%, and the mean conversion rate was calculated to be 400 mol propyne/gram atom Pd/hour.

EXAMPLE 10

The method of Example 1 was repeated, but using 0.2 mmol methanesulfonic acid instead of 1 mmol trifluoromethanesulfonic acid, and heating to 90° C. instead of 70° C. The selectivity to methyl methacrylate was calculated to be 96%, and the mean conversion rate was calculated to be 600 mol propyne/gram atom Pd/hour.

EXAMPLE 11

The method of Example 10 was repeated, but using 0.12 mmol 1,3-bis[di-(2-pyridyl)phosphino]propane instead of 1,3-bis[(2-pyridyl)phenylphosphino]propane. The selectivity to methyl methacrylate was calculated to be 98%, and the mean conversion rate was calculated to be 600 mol propyne/gram atom Pd/hour.

EXAMPLE 12

A 250 ml magnetically-stirred stainless steel autoclave was successively filled with 0.1 mmol palladium (II) acetate, 0.12 mmol bis[(2-pyridyl)phenylphosphino]propane, 1 mmol methanesulfonic acid and 50 ml methanol. Air was then evacuated from the autoclave, and then ethyne (1.4 bar) and carbon monoxide (30 bar) were added. The autoclave was then sealed and heated to a temperature of 75° C. After the reaction had ended, a sample of the contents of the autoclave was analysed by gas liquid chromatography. From the results of the analysis, the selectivity to methyl acrylate was calculated to be 83%, and the mean conversion rate was calculated to be 300 mol ethyne/gram atom Pd/hour. An interesting by-product, methyl 2,4-pentadienoate, was also found to have been formed with a selectivity of 17%.

EXAMPLE 13

The method of Example 12 was repeated, but using 1 mmol copper (II) tosylate instead of 1 mmol methanesulfonic acid, and heating to 90° C. instead of 75° C. The selectivity to methyl acrylate was calculated to be 82% (the remaining 18% being methyl 2,4-pentadienoate), and the mean conversion rate was calculated to be 200 mol ethyne/gram atom Pd/hour.

EXAMPLE 14

The method of Example 12 was repeated, but using 0.2 mmol p-toluenesulfonic acid instead of 1 mmol methanesulfonic acid, heating to 90° C. instead of 75° C., and using 60 bar carbon monoxide instead of 30 bar. The selectivity to methyl acrylate was calculated to be 92%, and the mean conversion rate was calculated to be about 100 mol ethyne/gram atom Pd/hour.

EXAMPLE 15

A 250 ml magnetically-stirred stainless steel autoclave was successively filled with 0.5 mmol nickel (II) acetate, 0.6 mmol bis[(2-pyridyl)phenylphosphino]propane 1 mmol trifluoromethanesulfonic acid and 50 ml n-butanol. Air was then evacuated from the autoclave, and then ethyne (1.4 bar) and carbon monoxide (50 bar) were added. The autoclave was then sealed and heated to a temperature of 125° C. After the reaction had ended, a sample of the contents of the autoclave was analysed by gas liquid chromatography. From the results of the analysis, the selectivity to n-butyl methacrylate was calculated to be 100%, and the mean conversion rate was calculated to be 100 mol ethyne/gram atom Ni/hour.

COMPARATIVE EXAMPLE 2

The method of Example 15 was repeated, but using 0.6 mmol bis-1,3-(diphenylphosphino)propane instead of 0.6 mmol bis [(2-pyridyl)phenylphosphino]propane. No acrylate product was obtained.

EXAMPLE 16

A 250 ml magnetically-stirred stainless steel autoclave was successively filled with 0.05 mmol palladium (11) acetate, 0.06 mmol 1,5-bis[(2-pyridyl)phenylphosphino]-3-oxapentane, 0.1 mmol p-toluenesulfonic acid and 50 ml methanol. Air was then evacuated from the autoclave, and then 30 ml propyne was added. Carbon monoxide was then added to a pressure of 60 bar. The autoclave was then sealed. During the ensuing reaction, heat was generated and the temperature rose to 35° C. After the reaction had ended, a sample of the contents of the autoclave was analyzed by gas liquid chromatography. From the results of the analysis, the selectivity to methyl methacrylate was calculated to be 99.2%, and the mean conversion rate was calculated to be 12,000 mol propyne/gram atom Pd/hour.

EXAMPLE 17

The method of Example 16 was repeated, but instead of adding 30 ml propyne, the autoclave was pressurized with 1.4 bar ethyne. Methyl acrylate was found to have been formed with a selectivity of 100%. The mean conversion rate was calculated to be 5,000 mol ethyne/gram atom Pd/hour.

EXAMPLE 18

The method of Example 16 was repeated, but using 30 ml methanol instead of 50 ml, and 30 ml phenylethyne instead of 30 ml propyne. During the reaction, the temperature inside the autoclave rose by 40° C. The selectivity to methyl phenacrylate was calculated to be 98.2%, and the mean conversion rate was calculated to be 50,000 mol phenylethyne/gram atom Pd/hour.

EXAMPLE 19

The method of Example 18 was repeated, but using 30 ml isopropanol instead of 30 ml methanol. After sealing the autoclave, the reaction contents were warmed, whereafter the reaction started and the temperature rose to 40° C. The selectivity to isopropyl acrylate was calculated to be 98.3% and the mean conversion rate was calculated to be 40,000 mol phenylethyne/gram atom Pd/hour.

EXAMPLE 20

The method of Example 19 was repeated, but using 0.025 mmol palladium (II) acetate instead of 0.05 mmol and heating to 35° C. The selectivity to isopropyl acrylate was calculated to be 98.4%, and the mean conversion rate was calculated to be 60,000 mol phenylethyne/gram atom Pd/hour.

EXAMPLE 21

The method of Example 20 was repeated, but using 0.06 mmol 1,8-bis[(2-pyridyl)phenylphosphino]-3,6-dioxaoctane instead of 0.06 mmol 1,5-bis[(2-pyridyl)-phenylphosphino]-3-oxapentane. The selectivity to isopropyl acrylate was calculated to be 99.4%, and the mean conversion rate was calculated to be 4,000 mol phenylethyne/gram atom Pd/hour.

EXAMPLE 22

The method of Example 16 was repeated, but using 0.06 mmol 1,8-bis[(2-pyridyl)phenylphosphino]-3,6-dioxaoctane instead of 0.06 mmol 1,5-bis[(2-pyridyl)-phenylphosphino]-3-oxapentane. Methyl methacrylate was formed with a selectivity of 99.6%. The mean conversion rate was 500 mol propyne/gram atom Pd/hour.

EXAMPLE 23

The method of Example 16 was repeated, but using 0.2 mmol benzenephosphonic acid instead of 0.1 mmol p-toluenesulfonic acid, and heating the contents of the autoclave to 40° C. The selectivity to methyl methacrylate was calculated to be 99.2%, and the mean conversion rate was calculated to be 2,000 mol propyne/gram atom Pd/hour.

EXAMPLE 24

The method of Example 23 was repeated, but using 0.2 mmol t-butylsulfonic acid instead of 0.2 mmol benzenephosphonic acid. The selectivity to methyl methacrylate was calculated to be 99.2%, and the mean conversion rate was calculated to be 3,000 mol propyne/gram atom Pd/hour.

EXAMPLE 25

The method of Example 23 was repeated, but using 0.2 mmol trifluoromethanesulfonic acid instead of 0.2 mmol benzenephosphonic acid. The selectivity to methyl methacrylate was calculated to be 99.2%, and the mean conversion rate was calculated to be 10,000 mol propyne/gram atom Pd/hour.

EXAMPLE 26

A 250 ml magnetically-stirred stainless steel autoclave was successively filled with 0.1 mmol palladium (II) acetate, 0.11 mmol 1,5-bis[(2-pyridyl)phenylphosphino]-3-oxapentane, 0.2 mmol p-toluenesulfonic acid, 30 ml methanol and 30 ml methyl methacrylate. Air was then evacuated from the autoclave, and then 30 ml propyne was added. Carbon monoxide was then added to a pressure of 60 bar. The autoclave was then sealed and heated to a temperature 30° C., whereupon an exothermic reaction took place, and the temperature increased by a further 50° C. After the reaction had ended, a sample of the contents of the autoclave was analyzed by gas liquid chromatography. From the results of the analysis, the selectivity to methyl methacrylate was calculated to be 98.6%, and the mean conversion rate was calculated to be 50,000 mol propyne/gram atom Pd/hour.

COMPARATIVE EXAMPLE 3

The method of Example 26 was repeated, but using 0.12 mmol 1,5-bis(diphenyl)phosphino-3-oxapentane instead of 0.11 mmol 1,5-bis[(2-pyridyl)phenylphosphino]-3-oxapentane, 50 ml methanol instead of 30 ml methanol and 30 ml methyl methacrylate, and heating to 80° C. The selectivity to methyl methacrylate was only 37%, and the mean conversion rate was only 50 mol propyne/gram atom Pd/hour.

What is claimed is:

1. A process for the preparation of alpha,beta-unsaturated carboxylic acids, alpha,beta-unsaturated carboxylic esters and alpha,beta-unsaturated anhydrides, which comprises reacting an acetylenically unsaturated compound with carbon monoxide and a hydroxyl-containing compound in the presence of a catalyst system consisting essentially of:
(a) a source of a Group VIII metal cation,
(b) a source of an organic diphosphine having at least one of the phosphorus atoms having an aromatic substituent containing an imino nitrogen atom, and
(c) a source of an anion.

2. The process as claimed in claim 1, wherein the source of a Group VIII metal cation i a Group VIII metal salt.

3. The process as claimed in claim 2, wherein the Group VIII metal is selected from the group consisting of nickel, palladium and platinum.

4. The process as claimed in claim 3, wherein the Group VIII metal is palladium.

5. The process as claimed in claim 1, wherein which the organic diphosphine has the general formula:

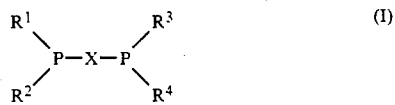

wherein which at least one of $R^1$, $R^2$, $R^3$ and $R^4$ represents an aromatic substituent containing an imino nitrogen atom, the remainder of $R^1$, $R^2$, $R^3$ and $R^4$ independently represent a substituted or unsubstituted hydrocarbyl or heterocyclic group, and X represents a divalent bridging group containing from 1 to 10 atoms in the bridge.

6. The process as claimed in claim 5, wherein said imino nitrogen atom in said aromatic substituent containing an imino nitrogen atom is connected to a phosphorus atom through a single linking carbon atom.

7. The process as claimed in claim 6, wherein the aromatic substituent containing an imino nitrogen atom is selected from a 2-pyridyl and a 2-pyrimidyl group.

8. The process as claimed in claim 5, wherein said divalent bridging group is selected from a hydrocarbon, an ether and a thio-ether residue.

9. The process as claimed in claim 8, wherein the divalent bridging group is a dialkyl ether residue.

10. The process as claimed in claim 5, wherein the remainder of $R^1$, $R^2$, $R^3$ and $R^4$ are selected from alkyl groups. substituted phenyl groups, and unsubstituted phenyl groups.

11. The process as claimed in claim 1, wherein the number of moles of phosphine per gram atom of Group VIII metal is in the range of from about 0.5 to about 5.

12. The process as claimed in claim 1, wherein the source of an anion is a protonic acid.

13. The process as claimed in claim 12, wherein the anion is a sulfonate.

14. The process as claimed in claim 1, wherein process is carried out at a temperature in the range of from about 10° C. to about 200° C.

15. The process as claimed in claim 1, wherein said process is carried out at a pressure in the range of from about 1 bar to about 70 bar.

16. The process as claimed in claim 1, wherein said acetylenically unsaturated compound is an alpha-alkyne having from 2 to about 10 carbon atoms.

17. The process as claimed in claim 1, wherein said hydroxyl-containing compound is an alkanol having from 1 to about 10 carbon atoms.

* * * * *